US012636068B2

(12) United States Patent
Cheng et al.

(10) Patent No.: US 12,636,068 B2
(45) Date of Patent: May 26, 2026

(54) COLORED VITREOUS ENAMEL COMPOSITION FOR ELECTROSURGICAL TOOL

(71) Applicant: Medtronic Advanced Energy LLC, Minneapolis, MN (US)

(72) Inventors: Xiaoming Cheng, Keller, TX (US); William X Siopes, Jr., Tyngsborough, MA (US); Zahedul Huq, Keller, TX (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 0 days.

(21) Appl. No.: 18/658,784

(22) Filed: May 8, 2024

(65) Prior Publication Data

US 2024/0293168 A1      Sep. 5, 2024

Related U.S. Application Data

(63) Continuation of application No. 16/327,210, filed as application No. PCT/US2017/061623 on Nov. 14, 2017, now abandoned.

(Continued)

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 18/1402* (2013.01);
(Continued)

(58) Field of Classification Search
CPC . A61B 18/1206; A61B 18/14; A61B 18/1402; A61B 18/148;
(Continued)

(56) References Cited

U.S. PATENT DOCUMENTS

| 4,732,794 A | 3/1988 | Hyde |
| 4,820,545 A | 4/1989 | Negrych |
| | (Continued) | |

FOREIGN PATENT DOCUMENTS

| DE | 102016111390 | 12/2017 |
| ES | 2350943 T3 | 1/2011 |

OTHER PUBLICATIONS

"ASM Standard Gloss Levels," 2020 (Year: 2020), 1 page.
(Continued)

*Primary Examiner* — Khadijeh A Vahdat
(74) *Attorney, Agent, or Firm* — Husch Blackwell LLP

(57) ABSTRACT

A colored (viz., not black) vitreous enamel coating for an electrosurgical metal cutting blade provides heat-resistant, durable blade coloration and facilitates differentiation or discrimination between, or identification of, different blades. Different colors may be employed on different blade shapes in an array of blades, on blades used for different surgical procedures, or on blades used on different tissue types. The color may be applied to a portion of a blade to denote an edge or other feature. The color may preferentially absorb the primarily blue-hued light emitted by an electrosurgery plasma and preferentially reflect light of other hues; make the blade more visible against surrounding tissues; or discourage reflection of visible or other light (e.g., infrared radiation) in colors that might interfere with markers, sensors or other instruments designed to measure light emitted by or passing through nearby tissue such as by transillumination.

21 Claims, 6 Drawing Sheets

Related U.S. Application Data

(60) Provisional application No. 62/421,895, filed on Nov. 14, 2016.

(51) Int. Cl.

| | |
|---|---|
| *A61L 31/02* | (2006.01) |
| *A61L 31/14* | (2006.01) |
| *C03C 3/064* | (2006.01) |
| *C03C 3/066* | (2006.01) |
| *C03C 3/091* | (2006.01) |
| *C03C 3/093* | (2006.01) |
| *C03C 4/02* | (2006.01) |
| *C03C 4/16* | (2006.01) |
| *C03C 8/02* | (2006.01) |
| *C03C 8/04* | (2006.01) |
| *C03C 8/14* | (2006.01) |
| *C03C 8/16* | (2006.01) |
| *C03C 10/00* | (2006.01) |
| *A61B 18/00* | (2006.01) |

(52) U.S. Cl.

CPC .......... *A61B 18/148* (2013.01); *A61L 31/026* (2013.01); *A61L 31/14* (2013.01); *C03C 3/064* (2013.01); *C03C 3/066* (2013.01); *C03C 3/091* (2013.01); *C03C 3/093* (2013.01); *C03C 4/02* (2013.01); *C03C 4/16* (2013.01); *C03C 8/02* (2013.01); *C03C 8/04* (2013.01); *C03C 8/14* (2013.01); *C03C 8/16* (2013.01); *C03C 10/00* (2013.01); *C03C 10/0036* (2013.01); *C03C 10/0054* (2013.01); *A61B 2018/00083* (2013.01); *A61B 2018/00107* (2013.01); *A61B 2018/00125* (2013.01); *A61B 2018/00148* (2013.01); *A61B 2018/00601* (2013.01); *A61B 2018/00607* (2013.01); *A61B 2018/1253* (2013.01); *A61B 2018/126* (2013.01); *A61B 2018/1412* (2013.01); *A61B 2018/1415* (2013.01); *C03C 2204/00* (2013.01)

(58) Field of Classification Search

CPC  A61B 2018/00083; A61B 2018/00107; A61B 2018/00125; A61B 2018/00148; A61B 2018/00601; A61B 2018/00607; A61B 2018/1253; A61B 2018/126; A61B 2018/1412; A61B 2018/1415; A61L 31/026; A61L 31/14; C03C 10/00; C03C 10/0036; C03C 10/0054; C03C 2204/00; C03C 3/064; C03C 3/066; C03C 3/091; C03C 3/093; C03C 4/02; C03C 4/16; C03C 8/02; C03C 8/04; C03C 8/14; C03C 8/16

See application file for complete search history.

(56) References Cited

U.S. PATENT DOCUMENTS

| | | | |
|---|---|---|---|
| 5,393,714 A | 2/1995 | Thometzek et al. | |
| 6,080,152 A | 6/2000 | Nardella et al. | |
| 6,569,510 B1 | 5/2003 | Menon et al. | |
| 6,712,817 B1 | 3/2004 | Goto et al. | |

| | | | |
|---|---|---|---|
| 2003/0129329 A1 | 7/2003 | Grossman | |
| 2004/0087939 A1 | 5/2004 | Eggers et al. | |
| 2004/0151745 A1 | 8/2004 | Zimmer et al. | |
| 2007/0005057 A1 | 1/2007 | Heim et al. | |
| 2008/0027428 A1* | 1/2008 | Palanker | A61B 18/1402 |
| | | | 606/45 |
| 2008/0108443 A1 | 5/2008 | Jinno et al. | |
| 2010/0009203 A1 | 1/2010 | Nageno et al. | |
| 2013/0065250 A1 | 3/2013 | Hubbard et al. | |
| 2013/0183489 A1 | 7/2013 | Cremer et al. | |
| 2014/0276770 A1 | 9/2014 | Ellman | |
| 2016/0157920 A1* | 6/2016 | Vayser | A61B 18/1402 |
| | | | 600/249 |
| 2016/0175060 A1 | 6/2016 | Park | |
| 2016/0225966 A1 | 8/2016 | Maloney et al. | |
| 2019/0112225 A1* | 4/2019 | Mix | C03C 3/087 |

OTHER PUBLICATIONS

Atlas Steels Grade Data Sheet 630 (17-4PH), Jan. 2008, Atlas Steels (Year: 2008).

Atlas_Steels_Proof_of_Date (Year: 2023).

Borosilicate Glass Proof of Date (Year: 2023), 2 pages Borosilicate Glass, Skyline Components, Retrieved from the Internet: <www.skylinecomponents.com/Borosilicate.html> on Jan. 11, 2023, 2 pages.

Borosilicate Glass, Aug. 15, 2011 (Year: 2011) "Borosilicate Glass," Skyline Components, LLC., Aug. 15, 2022, 1 page.

Borosilicate Material Properties Proof of Date (Year: 2023), 7 pages Borosilicate Material Properties, Adams & Chittenden Scientific Glass Coop, 2003, 7 pages.

Borosilicate Material Properties, Retrieved from the Internet: <https://adamschittenden.com/technical/material-prop>, Nov. 18, 2009, 1 page.

Ceramic Technology, Jiaju Li et al., p. 225, China Light Industry Press, Jun. 2006, edition 1. No English translation available Concise statement of relevance included in concurrently filed Supplemental Information Disclosure Statement transmittal.

Christopher Brace, Radiofrequency and microwave ablation of the liver, lung, kidney and bone: what are the differences, 2009 (Year: 2009).

Civil Engineering Materials, Xiuquan Ni et al., p. 281, Wuhan University Press, Jan. 2014, edition 1 No English translation available.

Civil Engineering Materials, Yamei Zhang et al., p. 279, Southeast University Press, Jan. 2013, edition 4 No English translation available.

Gloss and Sheen (and drywall finishing levels required); Master Painters Institute; http://paintinfo.com/mpi/approvesheen.shtml; Apr. 2, 2021 (Year: 2021).

Gloss Testing Equipment Angle Selection; https://www.linshangtech.com/tech/tech489.html; Oct. 15, 2019 (Year: 2019).

Linear Expansion Coefficients (Year: 2010) Temperature Expansion Coefficients, Retrieved from the Internet: <https://engineeringtoolbox.com/thermal-expansion>, May 10, 2010, 1 page.

Linear Expansion Coefficients Proof of Date (Year: 2023) Thermal Expansion—Linear Expansion Coefficients, The Engineering ToolBox, 7 pages, 2023.

Office Action from related EP Application No. 17808685.6, dated Oct. 4, 2022, 4 pgs.

Peter Hidnert, Thermal Expansion of Titanium, Feb. 1943 (Year: 1943).

Application and File History of U.S. Appl. No. 16/327,210, filed Feb. 21, 2019. Inventors Cheng et al.

* cited by examiner

GLASS MELTING 62 → QUENCH 64 → MILLING 66 → SLURRY MAKING 68 → WET COATING 70 → BINDER BURN-OUT 72 → GLASS FIRING 74 → GLASS CRYSTALLIZATION 76

60

5μm

COLORED VITREOUS ENAMEL COMPOSITION FOR ELECTROSURGICAL TOOL

CROSS-REFERENCE TO RELATED APPLICATIONS

This application is a continuation of U.S. application Ser. No. 16/327,210 filed Feb. 21, 2019, now abandoned, which is a National Phase entry of International Application Serial Number PCT/US2017/061623 filed Nov. 14, 2017 and entitled "COLORED VITREOUS ENAMEL COMPOSITION FOR ELECTROSURGICAL TOOL", which claims the benefit of U.S. Provisional Application Ser. No. 62/421,895 filed Nov. 14, 2016 and entitled "ENAMEL COMPOSITION FOR ELECTROSURGICAL TOOL", the disclosures of which are incorporated herein by reference in their entireties.

FIELD OF THE INVENTION

This invention relates to vitreous enamel compositions for coating electrosurgical cutting blades, and to the coated blades and methods for their manufacture and use.

BACKGROUND

Certain electrosurgical cutting equipment utilizes plasma energy to dissect tissue and coagulate blood vessels while producing minimal collateral damage to surrounding tissue. The cutting blade designed for the electrosurgical application often employs an insulating layer on a portion of the cutting blade to prevent energy from dispersing onto the bulk surface of the blade. Additionally, the insulating layer typically defines an uninsulated cutting edge (viz., an exposed electrode). The cutting edge, upon the introduction of a certain pattern of radiofrequency (RF) waveform, creates a substantially uniform and focused electrical field that upon contact with the cells in tissue forms a plasma-mediated discharge.

Despite improvements, there remains a need for even better vitreous enamel coatings for electrosurgical cutting blades. Such vitreous enamel coatings are disclosed and claimed herein.

SUMMARY

Conventional electrosurgical devices are available with blades having a variety of shapes and configurations to facilitate their use on particular tissues or in particular surgical procedures. The blades themselves can be rather small, and careful inspection may be needed to distinguish between them.

Some electrosurgical blades include an organic coating layer (e.g., of polytetrafluoroethylene (PTFE), polyurethane or silicone resin) disposed over the blade substrate. For example, electrosurgical blades available from Megadyne traditionally employ a green-tinted opaque PTFE coating, with the same shade of green being employed on all blades. The green coating has been made the subject of Trademark Registration No. 2021699. A uniform color may be used to identify the blade supplier, but does not differentiate between different blade shapes. Also, an organic coating may burn off during use, and may produce odors, smoke or volatile products of degradation or combustion that may be objectionable to a surgeon, other operator or other personnel in the operating theater.

Electrosurgical blades available from Medtronic traditionally employ a translucent black vitreous enamel coating, with a typical coating thickness of about 100 μm. Based on an understanding that black does not represent a color, these blades do not have a colored vitreous enamel coating. Typically, the degree of translucency is such that the underlying metal substrate, including grinding or polishing marks, can be seen through the coating. During use, light emitted by the plasma discharge may pass through the coating, strike the polished metal substrate, and be specularly reflected back through the coating. Depending on a nearby individual's angle of view, a specular second surface reflection from the underlying substrate may represent an objectionable source of glare.

Light penetrating a translucent vitreous enamel coating may also heat up the underlying metal substrate. Although some heating is inevitably part of the plasma discharge process, and although temperatures may reach as high as 800° C. at the cutting edge, it nonetheless is desirable to avoid excessive heating in order to prolong blade life and reduce deterioration of the vitreous enamel or other insulative coating.

Vitreous enamel coatings may be formed from a glass frit that is melted atop a metal substrate and optionally heat processed to alter the physical properties, crystallinity or other characteristics of the resulting vitreous enamel. In some embodiments, the coating is delivered onto the metal substrate through a slurry which is formed by combining glass frit powders, binder, and solvent. The binder and solvent can be initially burned off in a burn-out process and the coating subsequently fired at elevated temperatures to form the vitreous enamel insulating layer on the metal substrate.

Although color has not traditionally been deliberately imparted to vitreous enamel coatings for electrosurgical blades, coloration (e.g., prominent coloration) may be imparted to such coatings by employing additives or steps that result in selective absorption or scattering of specific visible wavelengths. The components of the glass frit and processing conditions are desirably selected to achieve a desired color and opacity.

The present invention thus provides in one aspect an article comprising:

(a) an electrosurgical cutting blade comprising a metal electrode, and (b) a colored vitreous enamel coating on at least a portion of the metal electrode.

The invention provides in another aspect a vitreous enamel coating comprising a colored glass formed from glass frit, wherein the coating is disposed on a metal electrode for an electrosurgical cutting blade.

The invention provides in yet another aspect a method comprising providing a colored vitreous enamel precursor, applying the vitreous enamel precursor onto at least a portion of a metal electrode suitable for use as an electrosurgical cutting blade, and firing the vitreous enamel precursor to form a colored vitreous enamel coating. In an embodiment, different vitreous enamel colors are employed on different blade types or blade shapes in an array of blades, or on blades used for different surgical procedures or on different tissue types, in order to facilitate easier discrimination between blades, procedures or tissues. In another embodiment, the same color is used on all blades in an array of blades from a particular manufacturer, and the color serves as a heat-resistant durable source identifier for products from that manufacturer.

The electrosurgical cutting blade with its colored vitreous enamel insulating layer may be connected to a power source on an electrosurgical generator. The invention thus provides in another aspect a method comprising intermittently supplying radiofrequency energy to an electrosurgical cutting blade having a colored vitreous enamel coating to create a plasma-mediated discharge.

In some embodiments of the above-described article, coating and methods, the vitreous enamel coating contains sufficient colored pigment or colorant, or has sufficient crystallinity, so that the underlying metal electrode is not visible through the coating under typical indoor illumination. In additional embodiments, the vitreous enamel coating contains sufficient colored pigment or colorant, or has sufficient crystallinity, so that a specular second surface reflection from the underlying metal electrode is not visible through the coating during plasma operation.

In some embodiments of the above-described article, coating and methods, the vitreous enamel coating includes a non-infrared-absorptive (e.g., infrared-reflective) colored inorganic pigment. Such pigments may reduce or discourage undesirable heating caused by absorption of infrared energy emitted by the plasma.

In some embodiments of the above-described article, coating and methods, the chosen color may be a color other than white. White coatings tend to have good infrared rejection, especially if made using titanium dioxide, but may also exhibit objectionable glare. In some embodiments the coating is a primary color (such as a red, green or blue color in an additive RGB color space). In some embodiments, the coating has a color other than white. In some embodiments, the coating has a color (e.g., yellow or orange) that preferentially absorbs the primarily blue-hued light emitted by the plasma and preferentially reflects light of other hues. In some embodiments, the coating has a color (e.g., lime green, or fluorescent yellow) that enhances visibility of the blade against nearby tissue. In some embodiments, the coating has a color that discourages reflection of visible or other light (e.g., infrared radiation) in colors that might interfere with markers, sensors or other instruments designed to measure light emitted by or passing through nearby tissue, e.g., by transillumination.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

The details of one or more embodiments of the invention are set forth in the description below. Other features, objects, and advantages of the invention will be apparent from the description, drawing, and from the claims.

BRIEF DESCRIPTION OF THE DRAWING

In the accompanying Drawing.

Like reference symbols in the various figures of the Drawing indicate like elements. The elements in FIG. 1 and FIG. 3 through FIG. 5 are not to scale.

SELECTED DEFINITIONS

Figure 1:
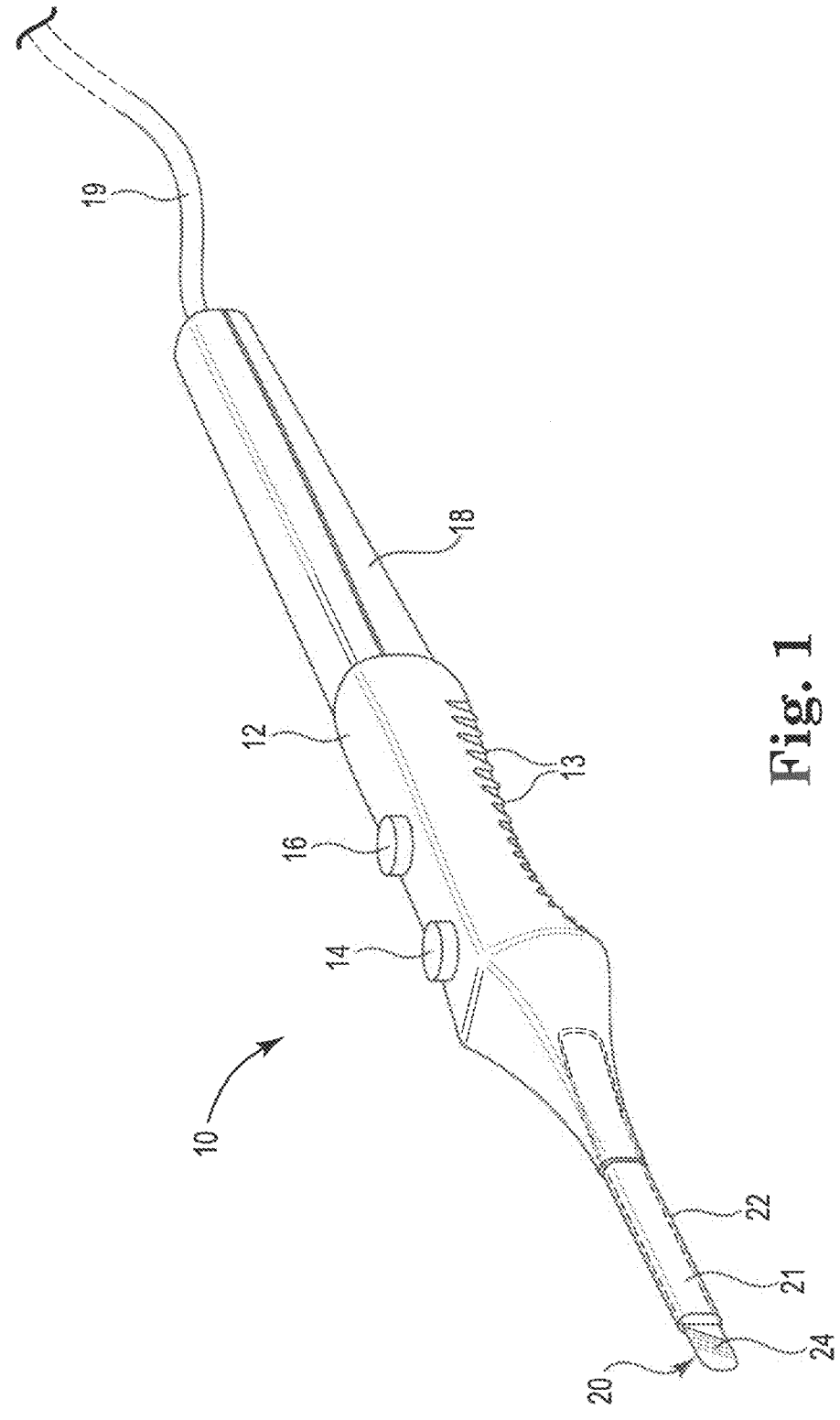
FIG. 1 is a perspective view of an electrosurgical cutting tool.

Unless otherwise specified, the following terms as used herein have the meanings provided below.

As used herein, "a," "an," "the," "at least one," and "one or more" are used interchangeably. Thus, for example, a coating composition that comprises "a" pigment can be interpreted to mean that the coating composition includes "one or more" pigments.

The term "amorphous" means a solid composition that lacks the order present in crystalline structures.

The terms "coefficient of thermal expansion" or "CTE" describes a thermomechanical property of a material and its ability to expand in size as the temperature is raised. For purposes of this disclosure, the CTE value is measured in accordance with ASTM E228-17, Standard Test Method for Linear Thermal Expansion of Solid Materials with a Push-Rod Dilatometer. The test heating rate is 5° C./min and the temperature range is from room temperature to about 1000° C. Those of ordinary skill in the art will recognize that the vitreous enamel is not tested after it is coated onto the metal electrode but rather the fired glass frit comprising the vitreous enamel is tested and corresponds to the CTE value of the vitreous enamel after coating and firing.

The terms "color" and "colored" mean having a hue (e.g., a primary color such red green or blue in an RGB additive color system, or a hue made by mixing two or more such primary colors) or a white coloration, but does not include a black coloration.

The term "crystalline" refers to a solid material that possesses a highly ordered or arranged structure, may in some circumstances form a crystal lattice, and may in some circumstances be opaque.

The terms "electrosurgical cutting tool" or "electrosurgical cutting blade" generally refer to the electrosurgical equipment use of plasma energy to dissect tissue or coagulate blood vessels while producing minimal collateral damage to surrounding tissue.

The terms "enamel" or "vitreous enamel" describe a transparent, semitransparent or opaque glassy substance applied to metallic or other hard surfaces, and capable of serving as a dielectric or insulating layer for an electrosurgical cutting blade.

The term "glass-ceramic" refers to a vitreous enamel composition that includes both an amorphous phase and a crystalline phase.

The term "glass frit" means the basic materials, often in particulate form, that may be wholly fused, for making glass or vitreous enamel.

The term "metal substrate" refers the metal electrode of an electrosurgical cutting tool that forms the cutting blade and provides a base upon which the vitreous enamel is applied.

The term "opaque" refers to a glass that reflects rather than refracts light in a wavelength range of interest (typically but not in all cases the visible light range from 400 to 700 nm).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The recitation of numerical ranges by endpoints includes all numbers subsumed within that range (e.g., 1 to 5 includes 1, 1.5, 2, 2.75, 3, 3.80, 4, 5, etc.). Furthermore, disclosure of a range includes disclosure of all subranges included within the broader range (e.g., 1 to 5 discloses 1 to 4, 1.5 to 4.5, 1 to 2, etc.).

DETAILED DESCRIPTION

As mentioned above, color has not traditionally been deliberately imparted to vitreous enamel coatings for electrosurgical blades. Color may however be imparted to such coatings by employing additives or steps that result in selective absorption or scattering of specific visible wavelengths. For example, inorganic light-absorbing or light-reflecting pigment particles having one or more colors may be dispersed into a glass. This may be done in a variety of ways, including adding the pigment particles to a glass frit from which a vitreous enamel will be prepared. In another embodiment, the pigment particles may be added to a slurry containing separately prepared milled glass particles together with a binder and optional solvent, followed by subjecting the slurry to a binder burnout step to remove the binder and optional solvent, followed by a firing step to form the vitreous enamel. The pigment particles desirably are more refractory than the glass so that they do not react with the glass during firing. The pigment particles may be used to impart color to a translucent or opalescent vitreous enamel. At a sufficiently high loading level, the pigment particles may provide an opaque vitreous enamel.

Color may also be imparted to a vitreous enamel by adding to the glass frit one or more colorants (e.g., certain metal oxides) that become a part of the glass and cause absorption of energy in a wavelength range of interest (e.g., the visible light range). Without intending to be bound by theory, such absorption may facilitate transition of electrons from an unfilled d or f orbital of lower energy to one of higher energy upon exposure of the vitreous enamel to energy in the desired wavelength range.

Color may also be imparted to a vitreous enamel by selecting suitable frit ingredients or suitably processing the molten enamel so as to form a visibly distinct crystalline phase that desired wavelengths of light, resulting in a colored appearance, or scatters all wavelengths of visible light, resulting in a white or off-white colored appearance.

If desired, the various approaches outlined above may be combined. For example, a variety of inorganic pigment particles and colorants may be combined with one another or with crystallization to obtain additional colors, and if desired increased opacity.

FIG. 1 depicts an embodiment of an electrosurgical cutting device 10. Device 10 includes an insulated handle 12 with hand (e.g., finger) grip ridges 13 as shown on the lower part thereof. This portion is intended to be held in the surgeon's hand (not shown in FIG. 1). Two control buttons 14, 16 activate electric switches (not shown in FIG. 1) which are provided for respectively selecting cutting or coagulation regimes. The rear portion 18 is for balance and for housing at least one cable 19 that may terminate in a conventional electrical connector (not shown in FIG. 1) for connection to a lead, leads or mating connector of a radiofrequency energy power supply (not shown in FIG. 1). The dimensions of the device of FIG. 1 are such that it is comfortably held in a hand, yet small enough for surgery for the intended application. The working end of the device of FIG. 1 includes at its distal end an electrosurgical cutting blade 20. Electrosurgical cutting blade 20 includes a metal substrate or electrode 21 housed in an intermediate portion or shaft 22. Intermediate portion 22 provides an insulated support that holds and extends the distal end of electrosurgical cutting blade 20 at an appropriate surgical viewing and cutting or coagulating distance from the surgeon's hand. The exposed distal portion of electrosurgical cutting blade 20 includes a colored vitreous enamel insulative coating 24. A non-limiting embodiment of an exemplary electrosurgical device is disclosed in U.S. Pat. No. 8,414,572 B2, herein incorporated by reference in its entirety.

As depicted in FIG. 1, device 10 has a single, flattened blade 20 fixedly mounted in intermediate portion 22. As will be appreciated by persons having ordinary skill in the art, the disclosed electrosurgical device may have a variety of other blade shapes and blade configurations, including blades with square edged, slant-edged, cylindrical, needle-like, bent, bendable or telescoping features. The disclosed electrosurgical device may be a monopolar device such as is shown in FIG. 1, or a bipolar device with two or more electrodes as may be used in some forms of electrosurgery.

In operation, the steps involved for cutting or otherwise operating on (e.g., coagulating) tissue with an electrosurgical device such as device 10 of FIG. 1 generally include contacting the tissue with a plasma generating electrode and applying an electric signal, having in some cases a low duty-cycle RF waveform, to the electrode. The signal causes the formation of a plasma discharge along the electrode between the electrode edge and the tissue and this plasma performs the tissue cutting or other operation.

The actual nature of the applied electrical signals which are suitable to create the desired plasma effect is well known in the field. For instance, in one embodiment the applied signal is an RF signal having a frequency in the range of 100 KHz to 10 MHz. Typically this energy is applied in the form of bursts of pulses. Each burst typically has a duration in the range of 10 microseconds to 1 millisecond. The individual pulses in each burst typically each have a duration of 0.1 to 10 microseconds with an interval therebetween of 0.1 to 10 microseconds. The actual pulses are typically square waves and bi-phasic, that is alternating positive and negative amplitudes. Generally the interval between pulses must be shorter than a lifetime of the plasma vapor cavity in order to maintain the cavity and the plasma regime during each pulse burst. In one embodiment the bursts are separated by a duration of at least one millisecond.

Figure 2:
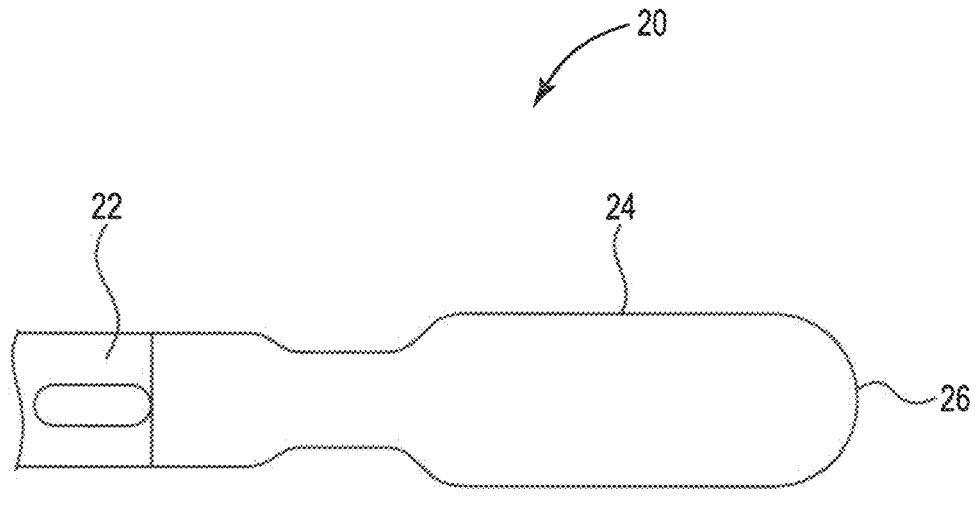
FIG. 2 is an orthogonal side view of a vitreous enamel-coated electrosurgical cutting blade.

The energy is delivered to the functional edge of the device through an electrosurgical cutting blade. FIG. 2 is an orthogonal side view of one embodiment of an electrosurgical cutting blade 20. The electrosurgical cutting blade 20 includes a metal electrode or substrate 22 at least a portion of which is coated with a colored, opaque vitreous enamel coating 24. An exposed edge 26 of the metal substrate 22, upon the introduction of radiofrequency energy, is capable of creating a substantially uniform and enhanced electrical field that upon contact with the cells in tissue forms the plasma medium. The vitreous enamel coating 24 functions as a non-conductive surface and thereby limits the formation of the plasma medium to the defined edge 26.

The chosen vitreous enamel coating coloration can serve one or more of a variety of functions, including identifying the blade manufacturer, making it easier for surgeons or other personnel to distinguish between different blades in an array of blades, identifying blades for use with particular surgical procedures or for use on particular tissues, making the blade more visible against nearby tissue or nearby fluids, absorbing light emitted by a nearby plasma-mediated discharge, reducing second surface reflections from an underlying metal electrode substrate, reducing glare caused by specular reflection from the plasma mediated discharge or lights in the operating field, and discouraging reflection of visible or other light (e.g., infrared radiation) in colors that might interfere with markers, sensors or other instruments designed to measure light emitted by or passing through nearby tissue, e.g., by transillumination.

Figure 3:
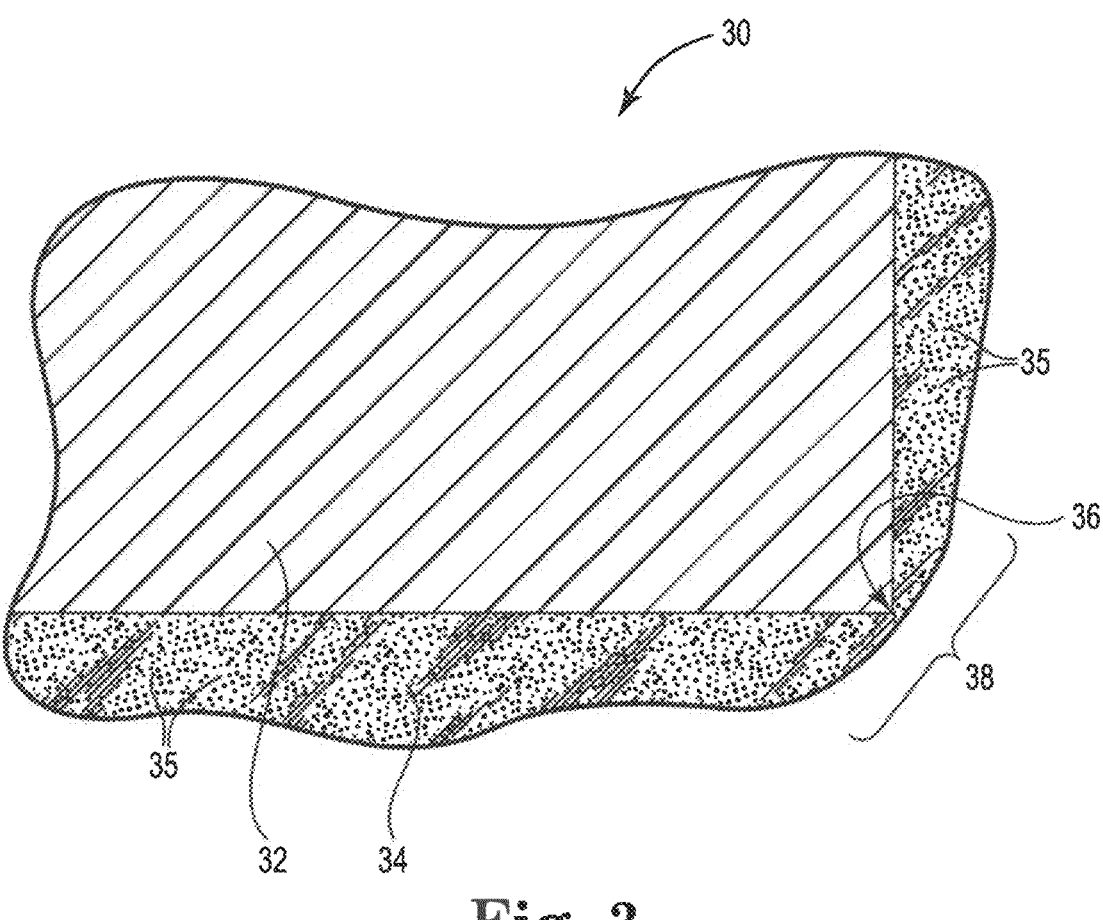
FIG. 3 is a cross-sectional schematic view of an edge portion of an electrosurgical cutting blade with a pigmented colored vitreous enamel coating.

FIG. 3 is a cross-sectional schematic view of an edge portion of a vitreous enamel-coated electrosurgical cutting blade 30. Blade 30 includes metal electrode substrate 32, colored vitreous enamel coating 34 containing refractory inorganic oxide pigment particles 35, and edge 36. Coating 34 may be amorphous or crystalline, but contains sufficient particles 35 so that coating 34 has a perceptible coloration.

Due to surface tension and other factors during application or firing of the frit from which coating 34 is made, coating 34 typically will have a reduced thickness near edge 36. In some embodiments, edge 36 may be exposed following firing. If desired, a mechanical impact, abrasive, electrical energy, acid etching or other measures may be used to remove a portion of, or to discourage the formation of, coating 34 proximate edge 36, thereby resulting in a region with reduced thickness or no coating at all proximate edge 36. Such reduced thickness or exposed edge provides a localized reduction in the breakdown voltage strength of coating 36 and helps promotes initial plasma formation and plasma maintenance proximate edge 36 when electromagnetic energy is applied to metal electrode 32.

In a preferred embodiment, coating 34 has a distinctive, easily perceptible coloration and a non-transparent (e.g., opaquely pigmented) appearance. In a further preferred embodiment, coating 34 contains sufficient pigment particles 35 so that substrate 32 is not visible through portions of coating 34 that are remote from edge 36 (viz., portions that are not adjacent to edge 36 and consequently do not have a reduced thickness) under normal indoor illumination. In another further preferred embodiment, coating 34 contains sufficient pigment particles 35 so that substrate 32 is not visible through such remote portions of coating 34 under the illumination provided by the plasma mediated discharge or under typical operating theater illumination. The pigment particles 35 in coating 34 consequently preferably reduce or eliminate unwanted second surface specular reflection of light traveling through (viz., into and out of) coating 34. Such light is instead preferentially absorbed or scattered (e.g., via diffuse reflection) by the pigment particles 35.

Coloration like that discussed above in connection with FIG. 3 may also be provided by adding to the glass frit one or more colorants (e.g., certain metal oxides) that become a part of the glass and cause absorption of energy in a wavelength range of interest (e.g., the visible light range). Such additives may be used in place of or in addition to the inorganic pigment particles 35, and when used by themselves may provide colors and a color gamut different from that available through the use of the inorganic pigment particles by themselves.

Figure 4:
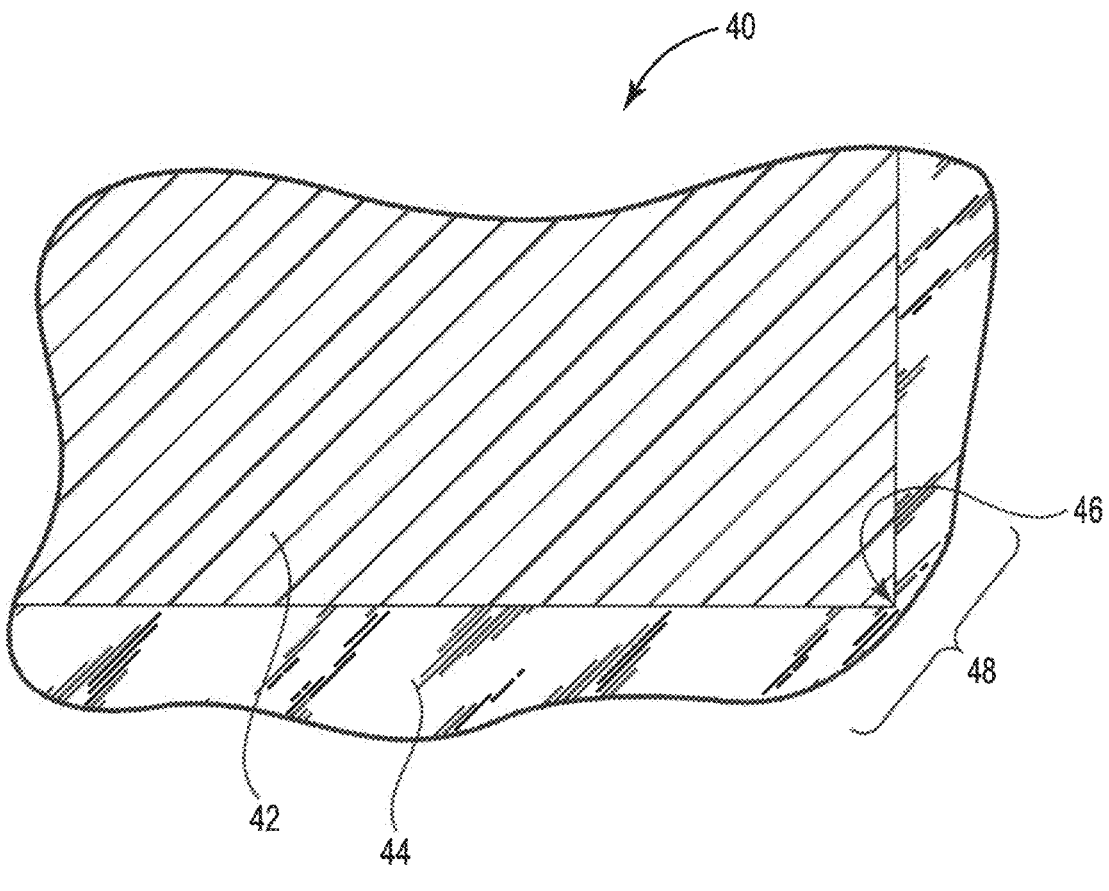
FIG. 4 is a cross-sectional schematic view of an edge portion of an electrosurgical cutting blade with an opaque colored vitreous enamel coating.

FIG. 4 is a cross-sectional schematic view of an edge portion of a vitreous enamel-coated electrosurgical cutting blade 40. Blade 40 includes metal electrode substrate 42, colored vitreous enamel coating 44, and edge 46. Blade 40 is similar to blade 30 in FIG. 3, and its coating 44 may contain pigment particles (not shown in FIG. 4, but like particles 35 if present), but coating 44 also contains sufficient crystallinity so that coating 44 has a perceptible coloration (e.g., a white or off-white coloration). In a preferred embodiment, coating 44 has a distinctive, easily perceptible coloration and a non-transparent (e.g., opaque) appearance. In a further preferred embodiment, coating 44 contains sufficient crystallinity so that substrate 42 is not visible through portions of coating 44 that are remote from edge 46 under normal indoor illumination. In another further preferred embodiment, coating 44 contains sufficient crystallinity so that substrate 42 is not visible through such remote portions of coating 44 under the illumination provided by the plasma mediated discharge or under typical operating theater illumination. The crystallinity in coating 44 consequently preferably reduces or eliminates unwanted second surface specular reflection of light traveling through (viz., into and out of) coating 44. Such light is instead preferentially absorbed or scattered (e.g., via diffuse reflection) by the presence of a crystalline phase or phases within coating 44.

Figure 5:
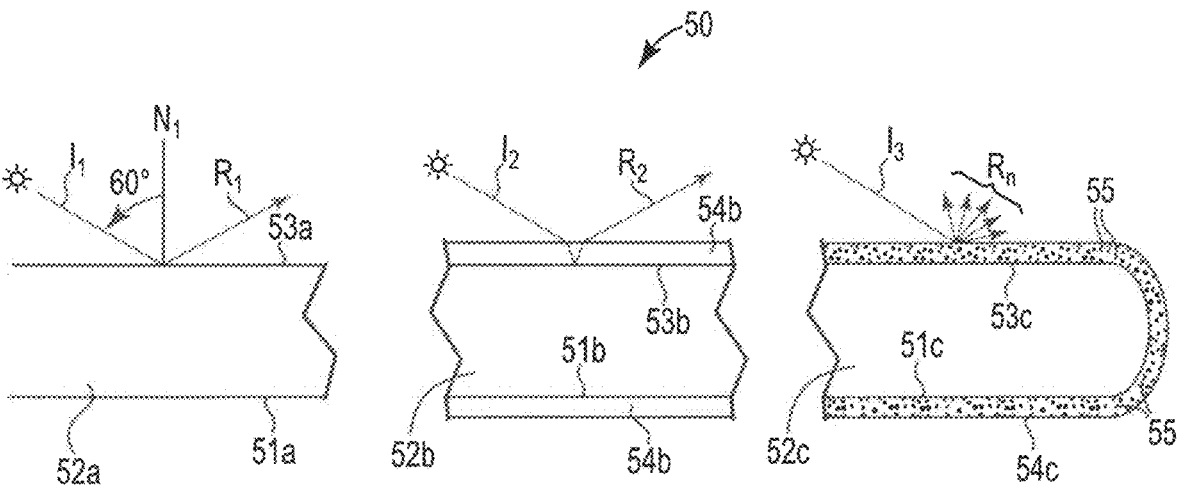
FIG. 5 is a cross-sectional schematic view of a portion of a coated electrosurgical cutting blade illustrating specular and diffuse reflection.

FIG. 5 is a cross-sectional schematic view of three portions of a coated electrosurgical cutting blade 50. Blade 50 is shown on the left of FIG. 5 with an uncoated metal substrate portion 52a having exposed upper and lower metal surfaces 51a and 53a, respectively; in the center of FIG. 5 with a coated metal substrate portion 52b having on its lower surface 51b and upper surface 53b an unfilled transparent or translucent layer of vitreous enamel coating 54b; and on the right of FIG. 5 with metal substrate portion 52c having on its lower surface 51c and upper surface 53c an opaque layer of vitreous enamel coating 54c filled with refractory inorganic particles 55 that impart color to layer 54c and scatter light. Different coatings are shown on substrate portions 52b and 52c. In a typical vitreous enamel coated electrosurgical blade, there may be an uncoated distal section like portion 52a, and a proximal portion bearing a vitreous enamel coating. Often the coating will be the same throughout, but this is not required. Different coatings, different-colored coatings, or a combination of colored and uncolored (e.g., black or transparent) coatings may be used on different portions of the blade. For example, in an asymmetric blade having a single sharpened edge, a distinctive colored or uncolored coating may be applied to regions remote from the edge, and a different distinctive colored or uncolored coating may be applied to a region encompassing the edge, so as to assist the surgeon in readily identifying the edge location.

Incident light ray $I_1$ is shown striking the upper surface 53a of substrate portion 52a at a 60° angle with respect to perpendicular (normal) dashed line $N_1$, and undergoing specular reflection as reflected ray $R_1$ travelling away from upper surface 53a at a similar 60° angle. Because the surface of an electrosurgical cutting blade is typically ground flat and may be highly polished, the reflected ray $R_1$ will typically be nearly as intense and nearly as focused as incident ray $I_1$.

Incident light ray $I_2$ is shown striking the upper surface of vitreous enamel coating 54b on substrate portion 52b at a 60° angle, undergoing refraction through coating 54b, striking and being specularly reflected away from upper surface 53b, passing back through coating 54b and emerging at a 60° angle from the upper surface of coating 54b as specular reflected light ray $R_2$. As was the case for rays $I_1$ and $R_1$, reflected ray $R_2$ may be nearly as intense and nearly as focused as incident ray $I_2$.

Incident light ray $I_3$ is shown striking the upper surface of vitreous enamel coating 54c on substrate portion 52c at a 60° angle. Due to the presence of refractory inorganic pigment particles 55 in coating 54c, incident ray $I_3$ is diffusely reflected away from coating 54c as reflected rays $R_n$. Reflected rays $R_n$ will present a less intense, unfocused appearance and exhibit much less glare than reflected rays $R_2$ and $R_3$.

The disclosed electrosurgical cutting blade includes a metal electrode that provides electrical connectivity to the power source and offers (or may be altered to offer) an exposed edge to enable the formation of plasma. Non-limiting examples of metals suitable to form electrodes include titanium, tantalum, molybdenum, tungsten, stainless steel, or alloys thereof. In some embodiments, the metal electrode can be cut or stamped from metal substrates. Secondary process steps such as etching, grinding or polishing may also be used on blades intended for use in certain surgical applications. The dimensions and shape of the metal electrode may also vary to accommodate different surgical applications. The metal electrode in some preferred embodiments possesses a CTE value from about 6, 8 or $10 \times 10^{-6}$/° C. up to about 11, 12, or $16 \times 10^{-6}$/° C.

The vitreous enamel may comprise a variety of glass or glass-ceramic materials. The selection of suitable glass or glass-ceramic materials will depend on several factors including, but not limited to, the end use surgical application, nearby illumination, blade design, expected temperatures during plasma formation, power voltage of the RF generator, water content of the tissue, and nature and extent of bonding to the metal substrate. In certain aspects, the glass or glass-ceramic composition may be selected to achieve a softening temperature that is near or preferably above the temperatures realized during plasma formation. For example, the softening temperature of a glass or glass-ceramic composition may be at least 500° C., at least 600° C. or at least 700° C. A softening temperature of at least 500° C. may in some circumstances enhance the durability of the glass. By increasing the softening temperature, the glass may withstand higher temperatures without softening and flowing during use.

The vitreous enamel may be created through the combination of various compounds to form certain types of glass. One embodiment includes the formation of an aluminoborosilicate glass with at least $SiO_2$, $B_2O_3$ and $Al_2O_3$ compounds. In a preferred aluminoborosilicate glass embodiment, the glass frit includes one or more alkaline earth oxides. Preferred such alkaline earth oxides include magnesium oxide (MgO), calcium oxide (CaO), strontium oxide (SrO) and barium oxide (BaO). Higher molecular weight alkaline earth oxides tend to provide higher CTE values. SrO is an especially preferred alkaline earth oxide for use in the disclosed aluminoborosilicate glasses.

As mentioned above, color can be imparted to the vitreous enamel in a variety of ways. For example, a variety of refractive inorganic pigments may be added to the disclosed vitreous enamel to provide coloration, light scattering, and in preferred embodiments an opaque coating. Exemplary such pigments include materials that may be classified as ceramic or refractory pigments, and which may contain elements such as cobalt (Co), chromium (Cr), copper (Cu), iron (Fe) and manganese (Mn). Exemplary commercially available pigments include BAYFERROX™, BAYOX-IDE™, COLORTHERM™ and LANXESS™ pigments from BASF, titanium dioxide pigments from DowDuPont, chromic oxide pigments from Elementis, phosphate ceramics from the ICL Group, and mineral-based pigments from Prince Minerals GmbH. The chosen pigment should be biocompatible, and consequently should avoid the use of potentially toxic metals (e.g., lead, cadmium and other materials that will be familiar to persons having ordinary skill in the art) and their oxides. In a preferred embodiment, the pigment is a non-infrared absorptive pigment. Exemplary such pigments include single or mixed metal oxides formed from a variety of metals, e.g., from aluminum, antimony, bismuth, boron, chromium, cobalt, gallium, indium, iron, lanthanum, lithium, magnesium, manganese, molybdenum, neodymium, nickel, niobium, silicon, tin, titanium, vanadium or zinc. Exemplary metal oxides include $Cr_2O_3$, $Al_2O_3$, $V_2O_3$, $Ga_2O_3$, $Fe_2O_3$, $Mn_2O_3$, $TiO_2$, $Ti_2O_3$, $In_2O_3$, $TiBO_3$, $NiTiO_3$, $MgTiO_3$, $CoTIO_3$, $ZnTiO_3$, $FeTiO_3$, $MnTiO_3$, $CrBO_3$, $NiCrO_3$, $FeBO_3$, $FeMoO_3$, $FeSn(BO_3)_2$, $BiFeO_3$, $AlBO_3$, $Mg_3Al_2Si_3O_{12}$, $NdAlO_3$, $LaAlO_3$, $MnSnO_3$, $LiNbO_3$, $LaCoO_3$, $MgSiO_3$, $ZnSiO_3$ and $Mn(Sb, Fe)O_3$. The metal oxide may have a corundum-hematite crystal lattice structure as described in U.S. Pat. No. 6,454, 848 B2, or may be a host component having a corundum-hematite crystalline structure which contains as a guest component one or more elements selected from aluminum, antimony, bismuth, boron, chromium, cobalt, gallium, indium, iron, lanthanum, lithium, magnesium, manganese, molybdenum, neodymium, nickel, niobium, silicon, tin, vanadium and zinc. A variety of non-infrared-absorptive pigments are commercially available, including mixed metal oxide pigments such as those supplied by Ferro Corporation (Cleveland, OH) under the COOL COLORS™ and ECLIPSE™ trademarks, for example V-778 COOL COLORS IR Black, V-780 COOL COLORS IR Black, V-799 COOL COLORS IR Black, 10201 ECLIPSE Black, 10202 ECLIPSE Black and 10203 ECLIPSE Black; mixed metal oxide pigments such as those supplied by Shepherd Color Company (Cincinnati, OH) under the ARTIC™ trademark, for example ARTIC Black 376, ARTIC Black 10C909, ARTIC Black 411 and ARTIC Black 30C940; and mixed metal oxide pigments such as those supplied by Tomatec America, Inc. (Florence, KY) under the numbers 42-707A and 707V10. The black pigments listed above, if used alone, would not be expected to provide a colored vitreous enamel coating. However, black pigments may be combined with colored pigments to obtain darkened shades. The selection of a particular pigment may depend in part upon the softening temperature of the vitreous enamel and the heat stability of the individual pigment. Not all pigments will have sufficient heat resistance to be used with all glass frits or with all glass powder firing steps. Sufficient pigment should be used to provide the desired degree of coloration while maintaining adequate processability and final properties in the vitreous enamel. Based on the final weight of the vitreous enamel, the vitreous enamel may for example contain at least about 0.1, at least about 0.2, at least about 0.5, at least about 1, at least about 5 or at least about 10 weight % pigment, and up to about 50, up to about 40, up to about 30 or up to about 20 weight % pigment.

As mentioned above, one or more colorants that become a part of the glass and cause absorption of energy in a wavelength range of interest may be added to the glass frit to provide coloration, light scattering, and in preferred embodiments an opaque coating in the final vitreous enamel. A variety of such colorants may be employed, and will be familiar to persons having ordinary skill in the glassmaking art. Exemplary colorants include many transition metals and lanthanides and their oxides. For example, $Co^{2+}$ ion absorbs light at wavelengths of about 500 to 700 nm and reflects blue light. Consequently, addition of cobalt oxide to the frit will impart a blue coloration to the vitreous enamel. Iron(II) oxide or chromium oxide may be employed to obtain bluish-green or green coloration. In borosilicate glasses rich in boron, sulfur imparts a blue color, and with calcium yields a deep yellow color. Manganese can be added to provide an amethyst or violet coloration, especially in the presence of sodium via formation of sodium permanganate. Copper oxide may be employed to obtain turquoise coloration. Nickel oxides may be used at various concentrations to obtain blue, violet, or black glass. Chromium oxide may be employed to obtain dark green or black coloration. Sufficient colorant should be used to provide the desired degree of coloration while maintaining adequate frit processability. Based on the final weight of the vitreous enamel, the vitreous enamel may for example contain at least about 0.1, at least about 0.2, at least about 0.5 or at least about 1 weight % colorant, and up to about 30, up to about 20, up to about 10 or up to about 5 weight % colorant.

As mentioned above, color may also be imparted to a vitreous enamel by selecting suitable frit ingredients or suitably processing the molten enamel so as to form a visibly distinct crystalline phase that scatters all wavelengths of light, resulting in a white or off-white colored appearance. If color is imparted to the vitreous enamel using other measures such as pigments or colorants as discussed above, then crystallinity is not necessary and the vitreous enamel composition may be an amorphous glass. However, in other embodiments the vitreous enamel composition includes a crystalline phase or additives that represent a crystalline phase. For example, the vitreous enamel may include a glass-ceramic composition. Glass-ceramic compositions may possess a crystalline phase along with the amorphous glass. The crystallinity of the vitreous enamel upon firing and formation may beneficially enhance the opacity and light-scattering or absorption behavior of the vitreous enamel. Non-limiting examples of crystalline phases include $Ca_2ZnSi_2O_7$ (hardystonite) or $Sr_2SiO_4$. Other combinations of compounds, such as nucleating agents, may be included in a glass frit and fired to create a glass-ceramic composition with at least a partial crystallinity that beneficially impacts the thermomechanical properties of the vitreous enamel-coated electrosurgical cutting blade. Crystallinity may also be imparted by adding to the glass frit one or more separate crystalline glass additives such as SIL-CEL™ 43 glass micro cellular fillers (from Silbrico Corporation, Hodkins, IL), FILLITE™ 100 ceramic spherical particles (from Trelleborg Fillite Inc., Norcross, GA), SPHERICEL™ hollow glass spheres (from Potter Industries Inc., Valley Forge, PA), 3M ceramic microspheres including grades G-200, G-400, G-600, G-800, W-210, W-410, and W-610 (from 3M, St. Paul, MN) or 3M hollow microspheres including 3M Performance Additives iM30K (also from 3M). Not all such crystalline glass additives will have sufficient heat resistance to be used with all glass frits. Sufficient crystallinity should be imparted to the vitreous enamel, or sufficient crystalline glass additive should be added to the glass frit, to provide the desired degree of coloration while maintaining adequate frit processability. When a crystalline glass additive is employed, and based on the final weight of the vitreous enamel, the vitreous enamel may for example contain at least about 0.1, at least about 0.2, at least about 0.5, at least about 1, at least about 5 or at least about 10 weight % crystalline glass additive, and up to about 50, up to about 40, up to about 30 or up to about 20 weight % crystalline glass additive. Expressed on a volume basis, the glass used to prepare the vitreous enamel preferably contains at least about 10, at least about 15, at least about 20, at least about 30, at least about 40, at least about 50 or at least about 60 volume percent crystalline phase(s).

The chosen glass compositions may include other compounds to impart or enhance certain features or characteristics such as glass transition temperature (Tg), nucleation, water resistance, diffuse reflection characteristics, CTE and dielectric properties. For example, the glass may include additives to impart to the glass a desired CTE as described in copending Application Serial No. PCT/US2017/061615, filed Nov. 14, 2017, or ingredients to reduce specular reflection characteristics and increase diffuse reflection characteristics as described in copending Application Serial No. PCT/US2017/061626, filed Nov. 14, 2017. Exemplary and non-limiting examples of other compounds that may be components of a glass frit to form the vitreous enamel include the alkaline earth oxides mentioned above, zinc oxide, magnesium oxide, sodium oxide, and potassium oxide. Such compounds may optionally be included in the glass frit at molar percentages ranging on a molar percentage from a trace, 0.1%, 1%, 2%, 5% or 10% up to about 5%, 10%, 15%20%, 30% or 40%. The frit desirably excludes materials that would not be biocompatible, for example lead or other toxic metals and their oxides. Exemplary glass frits and glasses include those from suppliers such as Elan Technology, Ferro Corporation, Mo-Sci Corporation and Schott AG. In a preferred embodiment, and before taking into account the addition of refractory pigments, colorants or crystalline glass additives as discussed above, a glass frit having the following compounds and molar percentages may be well suited for forming a vitreous enamel on an electrosurgical cutting blade: $SiO_2$ 30-50%, $B_2O_3$ 0.5-15%, $Al_2O_3$ 0.5-10%, SrO 5-30%, CaO 5-30%, and ZnO 0.5-20%.

Without being bound by theory, it is believed that the components in the disclosed vitreous enamel frit and vitreous enamel coating offer various attributes. For example, the function of each component in the glass composition may provide or offer certain features to the resulting enamel. The $Si_2O$ helps form the glass network. Modifiers such as alkali and alkaline earth oxides may increase the CTE value and potentially decrease the glass transition temperature. $Al_2O_3$ may modify the crystallization rate. Minor additives such as $TiO_2$ and $ZrO_2$ may act as nucleating agents. $B_2O_3$ may modify the extent and rate of crystallization and improve wetting of the glass to the metal substrate. $B_2O_3$ may also increase the vitreous enamel CTE. High CTE partially crystallizing systems may for example also include one or both of SrO and BaO. In some embodiments the vitreous enamel has a CTE of about $6\times10^{-6}/°$ C. to about $16\times10^{-6}/°$ C. and more preferably about $10\times10^{-6}/°$ C. to about $12\times10^{-6}/°$ C. The dielectric strength of the vitreous enamel coatings may vary and in preferred embodiments may be greater than about 20,000, about 30,000 or about 40,000 volts/mm (about 508, about 762 or about 1016 volts/mil) as measured using ASTM D149-09.

Figures 6, 7:
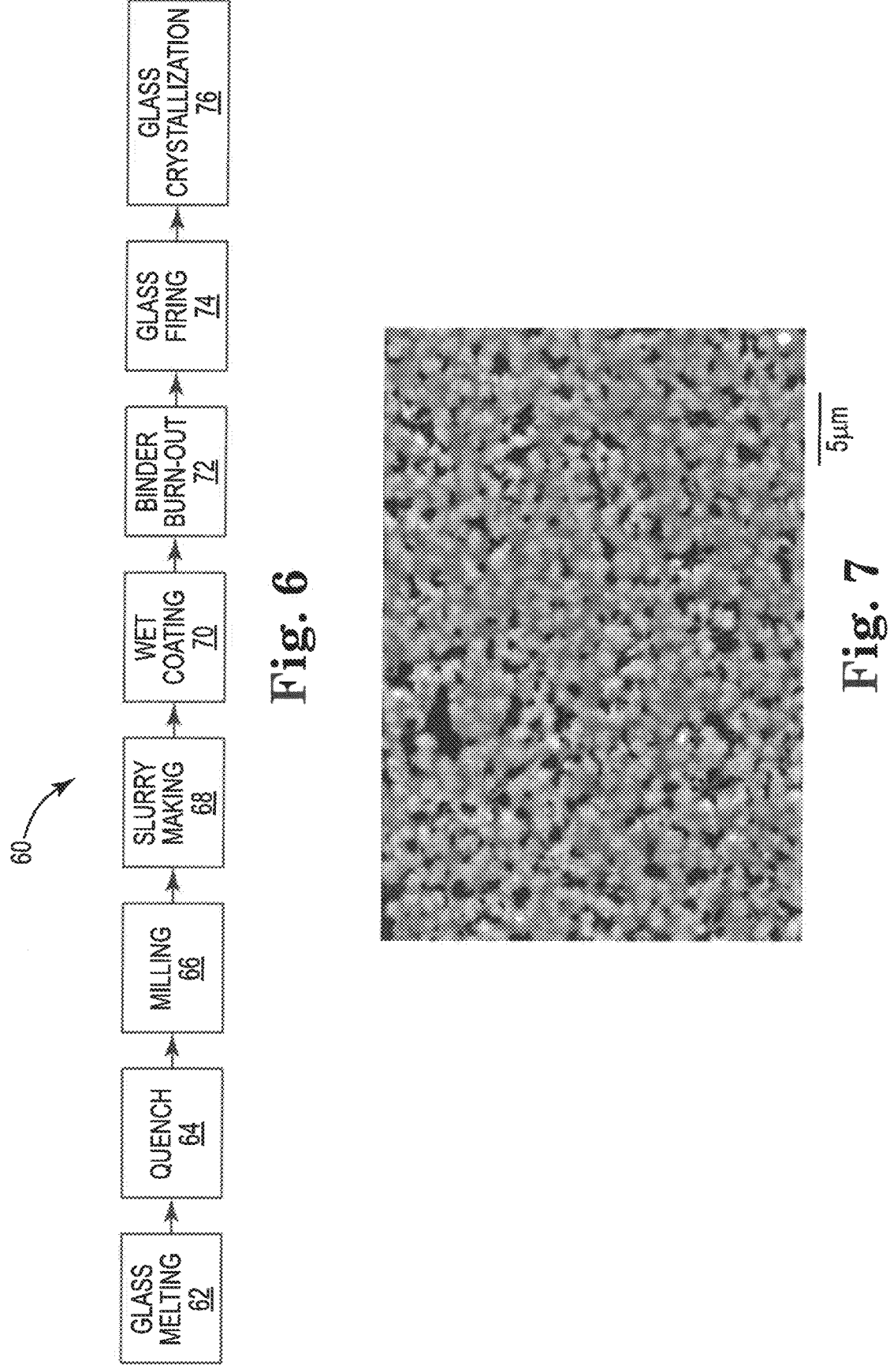
FIG. 6 is a schematic of one embodiment of a process for forming a vitreous enamel coating on an electrosurgical cutting blade.
FIG. 7 is a scanning electron microscope (SEM) image showing the crystalline structure of the vitreous enamel coating prepared in Example 5.

FIG. 6 is an illustration of one embodiment of a process 60 suitable for forming a vitreous enamel coating on an electrosurgical cutting blade from a glass frit. The frit may be separately-supplied or may be manually prepared just prior to use. Glass melting step 62 is typically performed by mixing and melting the frit components (including any refractory pigments, colorants or crystalline glass additives) in a furnace and quenching 64 the melt to form a solidified glass material. The resulting glass material is then milled 66 to a desired particle size that will support coating and formation of a vitreous enamel on the metal substrate. Those of ordinary skill in the art will recognize that particle size may have an impact on the properties of the resulting vitreous enamel. In certain embodiments, the particles may have a $d_{90}$ value between about 20 and about 50 μm (viz., 90 vol. % of the particles may in such embodiments have an average diameter below about 20 to below about 50 μm). In an optional wet coating step, a slurry 68 is prepared to facilitate the coating 70 of glass powder onto the metal substrate. The slurry may for example be prepared by dispersing the glass particles in a binder and carrier. The carrier can be any suitable solvent that is capable of maintaining a stable dispersion and a suitable viscosity for coating. Non-limiting examples of suitable carriers include mineral oil, ethanol, terpineol or combinations thereof. The binder enhances wet out and coating of the metal substrate during the coating process. Non-limiting examples of suitable binders include polyvinyl butyral, polyvinyl alcohol, and ethyl cellulose. Alternatively, the coating may be applied using a dry coating process, thereby alleviating the need for slurry formation. In any event, a variety of coating processes 70 may be employed. Non-limiting examples include electrophoretic deposition, dip coating, roll coating, spray coating or other similar application processes. The coating is preferably applied at a thickness sufficient to obtain a vitreous enamel coating that, after firing, will not unduly degrade during plasma formation and preferably will not suffer the defects that arise when using conventional vitreous enamel coatings. In a preferred embodiment, the metal substrate is coated to a vitreous achieve enamel coating thickness of about 75 μm to about 100 μm. In certain aspects in wet coating processes, the viscosity of the slurry may be controlled to address the coating thickness. Additionally, the coating is preferably applied in a manner that provides an exposed or only thinly-coated cutting edge. The edge may as discussed in connection with FIG. 3 be manually exposed by removing a portion of the vitreous enamel coating. The selection of a particular coating process may be dependent on various factors, including the metal substrate, the size and geometry of the cutting blade, and the type of glass frit, among others. Those of ordinary skill in the art will be capable of matching a particular coating process to achieve a desired enamel thickness on an electrosurgical cutting blade.

When using the slurry making step 68 and wet coating step 70 shown in FIG. 6, the binder and solvent are typically removed in a binder burn-out step 72. The electrosurgical cutting blade may be heated to a temperature and for a time sufficient to drive off any binder and solvent from the glass powder. The duration and temperature for this process may vary depending on the solvent or binder composition. In some embodiments, the temperature ranges up to about 500° C. for a time up to about 60 minutes. After this process, the remaining coating has green strength and ready for glass firing to form a vitreous enamel.

The glass firing process 74 encompasses ramping up the furnace temperature to the glass's firing temperature for a limited time to form the vitreous enamel, fuse it to the substrate, and anneal the final coating. Optionally, certain embodiments may allow for the formation of a crystalline phase 76. The firing generally takes place above 700° C. and in some embodiments above 750° C., or even above 800° C. The duration of the firing process and the time the coated substrate is held at temperature may for example vary depending upon the glass composition, coating thickness, type of metal substrate, blade shape and size, and other factors. Additionally, the let-down temperature may vary and may be staggered to enable solidification, annealing and stress relief. In certain embodiments, the annealing temperature is established at or above the Tg value for the selected vitreous enamel composition. The resulting vitreous enamel-coated electrosurgical cutting blade may for example be very similar in appearance to the embodiment shown in FIG. 2.

EXAMPLES

Examples 1 and 2

Colored vitreous enamel coatings on electrosurgical blades were prepared by combining ground glass, refractory inorganic pigments obtained from Prince Minerals, a solvent and dispersant in the amounts shown below in Table 1. The resulting mixtures were ball milled for about two hours to ensure an appropriate level of dispersion. The binder amount shown in Table 1 was added to the mixture and ball milled for about 4 hours to create a slurry. The viscosity of each slurry was measured using a Brookfield DV2T (LV) viscometer and spindle SC4-18/13R, and maintained above 1500 cp at 0.2 rpm. Each slurry was applied onto 420 stainless steel electrosurgical cutting blades using a dipping process. After the slurry coating was applied, the coated blades were subjected to burnout at about 600° C. for more than 60 minutes and subsequent firing at a temperature greater than 800° C. for more than 10 minutes. Upon the slow ramp down of the temperature to room temperature, the vitreous enamel-coated electrosurgical blades were visually inspected and photographed. Well-coated blades with distinctive blue (Example 1) and green (Example 2) coloration were obtained. The blades could easily be distinguished from one another based on the vitreous enamel color alone.

TABLE 1

| Ingredient | Example 1, wt. % | Example 2, wt. % |
|---|---|---|
| Sr—Ca—Zn—Al—B—Si alkaline earth aluminoborosilicate glass powder | 55.1 | 55.1 |
| P4055 blue pigment | 5.0 | |
| P4020 green pigment | | 5.0 |
| Toluene/ethanol solvent mixture | 16.2 | 16.2 |
| Triethyl phosphate dispersant | 1.1 | 1.1 |
| Ethyl cellulose binder | 22.6 | 22.6 |
| Total | 100 | 100 |

Example 3

A Sr—Ca—Zn—Al—B—Si alkaline earth aluminoborosilicate glass like that employed in Examples 1 and 2 was prepared, but the initial frit was modified by adding 2.36 wt. % cobalt oxide. Following melting of the frit and grinding of the resulting glass to form glass powder, a vitreous enamel-coated electrosurgical blade was prepared using the method of Example 1 but without addition of the refractory blue inorganic pigment. A well-coated blade with a distinctive blue coloration like that obtained in Example 1 was obtained.

Example 4

Coated blades with an even more intense coloration could be obtained by using the blue glass prepared in Example 3 as the glass powder in the blue-pigmented Example 1 slurry or green-pigmented Example 2 slurry.

Example 5

Following the glass melting step, the glass employed in Examples 1 and 2 was fired at 800° C., 830° C., 850° C. and 870° C. for 15 minutes at each of these temperatures. This produced a glass having two crystalline phases that scattered light at all visible wavelengths. A vitreous enamel-coated electrosurgical blade was prepared using the method of Example 1 but without addition of the refractory blue inorganic pigment. A well-coated blade with a distinctive white coloration was obtained. FIG. 7 is an SEM image showing the crystalline structure of the vitreous enamel coating.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. An electrosurgical cutting tool comprising:
   (a) an electrosurgical cutting blade comprising a metal electrode configured to generate plasma during an electrosurgical procedure at an edge of the metal electrode for cutting tissue, and
   (b) a colored vitreous enamel coating on at least a portion of the metal electrode, wherein the colored vitreous enamel coating is not black, has a color other than white, is configured to absorb light emitted by the plasma, configured to reduce glare caused by specular reflection of the plasma during the electrosurgical procedure, and contains sufficient colored pigment or colorant, or has sufficient crystallinity, so that a specular second surface reflection from the metal electrode is not visible through the colored vitreous enamel coating during the electrosurgical procedure.

2. The electrosurgical cutting tool of claim 1, wherein the colored vitreous enamel coating has a red color.

3. The electrosurgical cutting tool of claim 1, wherein the colored vitreous enamel coating has a green color.

4. The electrosurgical cutting tool of claim 1, wherein the colored vitreous enamel coating has a blue color.

5. The electrosurgical cutting tool of claim 1, wherein the colored vitreous enamel coating has a yellow color.

6. The electrosurgical cutting tool of claim 1, wherein the colored vitreous enamel coating has an orange color.

7. The electrosurgical cutting tool of claim 1, wherein the colored vitreous enamel coating has a lime green or fluorescent yellow color that enhances visibility of the electrosurgical cutting blade against nearby tissue.

8. The electrosurgical cutting tool of claim 1, wherein the colored vitreous enamel coating is configured to reduce glare under typical indoor illumination.

9. The electrosurgical cutting tool of claim 1, wherein the colored vitreous enamel coating is configured to reduce reflection of infrared radiation during the electrosurgical procedure compared to reflection of such infrared radiation through a translucent vitreous enamel coating on the metal electrode.

10. The electrosurgical cutting tool of claim 1, wherein the colored vitreous enamel coating contains sufficient colored pigment or colorant to reduce specular second surface reflections from the metal electrode.

11. The electrosurgical cutting tool of claim 1, wherein the colored vitreous enamel coating is configured to reduce reflection of visible or other light that interferes with one or more markers, sensors, or other instruments that measure light emitted by or passing through nearby tissue compared to reflection of such visible or other light through a translucent vitreous enamel coating on the metal electrode.

12. The electrosurgical cutting tool of claim 1, wherein the colored vitreous enamel coating is an amorphous glass composition.

13. The electrosurgical cutting tool of claim 1, wherein the colored vitreous enamel coating contains a crystalline phase that imparts such color to the colored vitreous enamel coating.

14. The electrosurgical cutting tool of claim 1, wherein the colored vitreous enamel coating contains at least 20 volume percent of a crystalline phase.

15. The electrosurgical cutting tool of claim 1, wherein the colored vitreous enamel coating comprises an aluminoborosilicate glass.

16. The electrosurgical cutting tool according to claim 1 wherein the colored vitreous enamel coating is formed from a glass frit comprising, as molar percentages:
   $SiO_2$ 30-50%,
   $B_2O_3$ 0.5-15%,
   $Al_2O_3$ 0.5-10%,
   SrO 5-30%,
   CaO 5-30%, and
   ZnO 0.5-20%.

17. An array of electrosurgical cutting tools of claim 1, wherein the electrosurgical cutting tools have the colored vitreous enamel coatings in different colors to enable surgeons or other personnel to distinguish between different electrosurgical cutting blades in the array.

18. An array of electrosurgical cutting tools of claim 1, wherein the electrosurgical cutting tools have the colored vitreous enamel coatings in different colors to enable surgeons or other personnel to identify different electrosurgical cutting blades for use with particular surgical procedures.

19. An array of electrosurgical cutting tools of claim 1, wherein the electrosurgical cutting tools have the colored vitreous enamel coatings in different colors to enable surgeons or other personnel to identify different electrosurgical cutting blades for use on particular tissues.

20. The electrosurgical cutting tool of claim 1, wherein the colored vitreous enamel coating facilitates one or more of blade or edge identification, blade differentiation, blade visibility, or avoiding interference with other instruments during electrosurgery.

21. The electrosurgical cutting tool of claim 1, wherein the colored vitreous enamel coating absorbs the primarily blue-hued light emitted by an electrosurgery plasma and reflects light of other hues.

\* \* \* \* \*